United States Patent
Burke, Jr. et al.

[11] Patent Number: 5,259,966
[45] Date of Patent: Nov. 9, 1993

[54] LOW CHLORINE OVERBASED CALCIUM SALTS

[75] Inventors: Frank D. Burke, Jr., Mentor; Jack L. Karn, Richmond Heights; Jody A. Kocsis, Chagrin Falls, all of Ohio

[73] Assignee: The Lubrizol Corporation, Wickliffe, Ohio

[21] Appl. No.: 974,046

[22] Filed: Nov. 10, 1992

[51] Int. Cl.$^5$ .............. C10M 159/24; C10M 159/22; C10M 159/20
[52] U.S. Cl. .................. 252/18; 252/33; 252/33.6; 252/39
[58] Field of Search .............. 252/18, 33, 33.6, 39

[56] References Cited

U.S. PATENT DOCUMENTS

| | | | |
|---|---|---|---|
| 3,155,617 | 11/1964 | Voorhees | 252/33.2 |
| 3,256,186 | 6/1966 | Greenwald | 252/18 |
| 3,372,116 | 3/1968 | Meinhardt | 252/36 |
| 3,493,516 | 2/1970 | Allphin et al. | 252/33.3 |
| 3,544,463 | 12/1970 | Koft, Jr. | 252/40.7 |
| 3,595,790 | 7/1971 | Norman et al. | 252/32.7 |
| 3,691,076 | 9/1972 | Chafetz et al. | 252/42.7 |
| 4,049,560 | 9/1977 | Dominey | 252/33.3 |
| 4,129,589 | 12/1978 | Eliades et al. | 260/504 |
| 4,206,062 | 6/1980 | Derbyshire et al. | 252/33.2 |
| 4,597,880 | 7/1986 | Eliades | 252/33.4 |
| 4,698,170 | 10/1987 | Le Coent | 252/33.2 |

FOREIGN PATENT DOCUMENTS 8718014 6/1989 France.

Primary Examiner—Prince Willis, Jr.
Assistant Examiner—Edna Wong
Attorney, Agent, or Firm—David M. Shold

[57] ABSTRACT

Overbased calcium salts, low in chloride content, are prepared using as a promoter a mixture of an alcohol and an inorganic calcium salt other than chloride which is soluble in the alcohol mixture.

20 Claims, No Drawings

LOW CHLORINE OVERBASED CALCIUM SALTS

BACKGROUND OF THE INVENTION

The present invention relates to an improved process for preparation of overbased materials, providing materials which are low in chlorine content.

Overbased materials have been long known and are important lubricating oil additives. These materials are metal salts of acidic organic compounds. Overbased materials are single phase, homogeneous, and generally Newtonian systems characterized by a metal content in excess of that which would be present according to the stoichiometry of the metal and the particular acidic organic compound reacted with the metal. Such materials are often prepared by mixing together an oil-soluble acid material, greater than 1 equivalent of base, such as a calcium base, and a promoter. Often the promoter includes an inorganic halide such as calcium chloride. This material is referred to as a co-promoter, and is believed to function by increasing the solubility of a calcium base (such as calcium hydroxide) in the reaction medium. In some cases the overbased material is further reacted with an acidic gas such as carbon dioxide. The following patents generally illustrate this and other related processes:

U.S. Pat. No. 3,256,186, Greenwald, Jun. 14, 1966, discloses a process for producing carbonated basic metal compositions. The process comprises carbonating a mixture of (A) one equivalent of an acidic substance, (B) at least about 0.1 equivalent of an alcohol per equivalent of (A), (C) from about 0.1% to about 5% by weight of (A) of an inorganic halide selected from the class consisting of ammonium halides, alkali metal halides, and alkaline earth metal halides, and (D) at least about 2 equivalents of an alkaline earth metal base per equivalent of (A). Especially useful as (B) are mixtures of methanol with a higher monohydric alcohol. Chlorides of ammonium, sodium, barium, and calcium are especially effective as (D).

U.S. Pat. No. 3,372,116, Meinhardt, Mar. 5, 1968, discloses preparation of basic metal phenates and salicylates. It discloses treatment of a polyisobutene-substituted phenol in mineral oil with calcium oxide, propanol, and acetic acid, followed by contacting with carbon dioxide. It also discloses treatment of a material with a mixture of methanol, amyl alcohol, and isobutyl alcohol containing calcium hydroxide and calcium acetate, followed by treatment with carbon dioxide. It lists suitable promoters as including carboxylic acids containing about 1-100 carbon atoms and metal salts thereof. Suitable monocarboxylic acids include formic, acetic, propionic, butyric acids, and so on.

U.S. Pat. No. 4,597,880, Eliades, Jul. 1, 1986, discloses a one-step process for preparation of overbased calcium sulfonate greases. The essential ingredients in the process include a liquid carrier, a sulfonic acid, calcium oxide or hydroxide, water-soluble carboxylic acids including acetic acid, preferably an alcohol or alkoxyalcohol of 1 to 8 carbon atoms, such as methanol or methyl (or ethyl) cellosolve, and water; the mixture is carbonated.

U.S. Pat. No. 3,155,617, Voorhees, Nov. 3, 1964, discloses a means of activating calcium oxide (prepared from roasting calcium carbonate), so that it is useful in the methanol process for preparing dispersions of calcium carbonate. The calcium oxide is treated in methanol suspension with a small amount of an acid such as HCl, sulfamic acid, $H_2SO_4$, $HNO_2$, $HNO_3$, or various organic acids such as acetic acid.

It is not always desirable, however, to have chloride present in an overbased material, because of its potentially corrosive properties and because of environmental concerns about residual chlorine in waste oils. Accordingly, the present invention provides an efficient process for preparing overbased materials which does not require the use of chloride-containing promoters or co-promoters.

SUMMARY OF THE INVENTION

The present invention provides a process for preparing an overbased calcium salt, comprising mixing together:

(A) an oil-soluble acid material;
(B) a promoter comprising:
  (i) an alcohol or alcohol mixture, and
  (ii) an inorganic calcium salt other than chloride which is soluble in the alcohol mixture of (i), or an acid or salt which forms said inorganic calcium salt when treated with a calcium base; and
(C) greater than 1 equivalent of a calcium base per equivalent of oil-soluble acid material.

The present invention also provides the material prepared by such a process.

DETAILED DESCRIPTION OF THE INVENTION

The overbased materials prepared by the present process are substantially free from chlorine. They may also be made, of course, substantially free from all halogens by selecting a promoter and co-promoter which is not only substantially free from chloride, but also substantially free from other halogens.

The present process includes mixing together an oil-soluble acid material, a promoter comprising an alcohol or alcohol mixture, and an inorganic calcium salt other than chloride which is soluble in the alcohol or alcohol mixture or an acid or salt which forms said inorganic calcium salt when treated with a calcium base, and greater than 1 equivalent of a calcium base per equivalent of oil-soluble acid material.

By the term "acid material" is meant not only the traditional acids such as carboxylic acids, phosphorus-containing acids, sulfonic acids, and phenols (i.e. aromatic hydroxy compounds) but also other materials which have replaceable hydrogens, including amides and even some alcohols. Preferably, the oil soluble acid material is a carboxylic acid or sulfonic acid with sulfonic and salicylic acids being more preferred. Throughout this specification and in the appended claims, any reference to acids, such as carboxylic, or sulfonic acids, is intended to include the acid-producing derivatives thereof such as anhydrides, lower alkyl esters, acyl halides, lactones and mixtures thereof unless otherwise specifically stated. Normally the use of acids or acid-producing derivatives which contain chlorine will be avoided, in order to aid in preparing a composition with a low overall chlorine content. However, the use of such materials is not absolutely excluded and in some cases may even be desirable.

The carboxylic acids useful in making the overbased salts of the invention may be aliphatic or aromatic, mono- or polycarboxylic acids. These carboxylic acids include lower molecular weight carboxylic acids (e.g., carboxylic acids having up to 22 carbon atoms such as acids having 4 to 22 carbon atoms or tetrapropenyl-substituted succinic anhydride) as well as higher molecular weight carboxylic acids.

The carboxylic acids of this invention are preferably oil-soluble. Usually, in order to provide the desired oil-solubility, the number of carbon atoms in the carboxylic acid should be at least 8, more preferably at least 18, more preferably at least 30, more preferably at least 50. Generally, these carboxylic acids do not contain more than 400 carbon atoms per molecule.

The lower molecular weight monocarboxylic acids contemplated for use in this invention include saturated and unsaturated acids. Examples of such useful acids include dodecanoic acid, decanoic acid, oleic acid, stearic acid, linoleic acid, tall oil acid, etc. Mixtures of two or more such agents can also be used.

Illustrative carboxylic acids include palmitic acid, stearic acid, myristic acid, oleic acid, linoleic acid, behenic acid, hexatriacontanoic acid, tetrapropylenyl-substituted glutaric acid, polybutenyl-substituted succinic acid derived from a polybutene (Mn=200-1500, preferably 300-1000), polypropenyl-substituted succinic acid derived from a polypropene, (Mn=200-1000, preferably 300-900), octadecyl-substituted adipic acid, chlorostearic acid, 9-methylstearic acid, dichlorostearic acid, stearyl-benzoic acid, eicosanyl-substituted naphthoic acid, dilauryl-decahydronaphthalene carboxylic acid, mixtures of any of these acids, their alkali and alkaline earth metal salts, and/or their anhydrides. A preferred group of aliphatic carboxylic acids includes the saturated and unsaturated higher fatty acids containing from 12 to 30 carbon atoms. Illustrative of these acids are lauric acid, palmitic acid, oleic acid, linoleic acid, linolenic acid, oleostearic acid, stearic acid, myristic acid, and undecylenic acid, alpha-chlorostearic acid, and alpha-nitrolauric acid.

Alternatively, the carboxylic acid can be an alkylalkyleneglycol-acetic acid, more preferably alkylpolyethyleneglycol-acetic acid. Such acids are available commercially from Sandoz Chemical under the tradename Sandopan TM acids.

In another embodiment, the carboxylic acids can be aromatic carboxylic acids. Examples of aromatic carboxylic acids include substituted and non-substituted benzoic, phthalic and salicylic acids or anhydrides. Preferably the substitution on the aromatic acids is such that the acid molecules contain at least an average of 12 aliphatic carbon atoms in an aliphatic hydrocarbon substituents per acid molecule. Overbased salts prepared from salicylic acids wherein the aliphatic hydrocarbon substituents are derived from polymerized lower 1-mono-olefins such as polyethylene, polypropylene, polyisobutylene, ethylene/propylene copolymers and the like and having average carbon contents of 30 to 400 carbon atoms are particularly useful. The above aromatic carboxylic acids are well known or can be prepared according to procedures known in the art.

Sulfonic acids useful in making the overbased salts in the process of the invention include the sulfonic and thiosulfonic acids. Generally they are salts of sulfonic acids. The sulfonic acids include the mono- or polynuclear aromatic or cycloaliphatic compounds. Examples of sulfonic acids are alkyl, alkenyl, alkoxyalkyl, carboalkoxyalkyl sulfonic acids. Specific examples of such acids are those having alkyl groups derived from petrolatum, saturated and unsaturated paraffin wax, and the polyalkenes. The sulfonic acids can also contain other inorganic or organic substituents in addition to those enumerated above such as, for example, hydroxy, mercapto, halogen, nitro, amino, nitroso, sulfide, disulfide, etc.

Illustrative examples of these sulfonic acids include monoeicosanyl-substituted naphthalene sulfonic acids, dodecylbenzene sulfonic acids, didodecylbenzene sulfonic acids, dinonylbenzene sulfonic acids, cetylchlorobenzene sulfonic acids, dilauryl beta-naphthalene sulfonic acids, the sulfonic acid derived by the treatment of polybutene having a number average molecular weight (Mn) in the range of 500 to 5000, preferably 800 to 2000, more preferably about 1500 with chlorosulfonic acid, nitronaphthalene sulfonic acid, paraffin wax sulfonic acid, cetyl-cyclopentane, sulfonic acid, lauryl-cyclohexane sulfonic acids, polyethylenyl-substituted sulfonic acids derived from polyethylene (Mn=300-1000, preferably 750), etc. Normally the aliphatic groups will be alkyl and/or alkenyl groups such that the total number of aliphatic carbons is at least 8, preferably at least 12 up to 400 carbon atoms, preferably 250.

Another group of sulfonic acids are mono-, di-, and tri-alkylated benzene and naphthalene (including hydrogenated forms thereof) sulfonic acids.

Specific examples of oil-soluble sulfonic acids are mahogany sulfonic acids; bright stock sulfonic acids; sulfonic acids derived from lubricating oil fractions having a Saybolt viscosity from 100 seconds at 100° F. to 200 seconds at 210° F.; petrolatum sulfonic acids; mono- and poly-wax-substituted sulfonic and polysulfonic acids of, e.g., benzene, naphthalene, phenol, diphenyl ether, naphthalene disulfide, etc.; other substituted sulfonic acids such as alkyl benzene sulfonic acids (where the alkyl group has at least 8 carbons), cetylphenol mono-sulfide sulfonic acids, dilauryl beta naphthyl sulfonic acids, and alkaryl sulfonic acids such as dodecyl benzene "bottoms" sulfonic acids. Dodecyl benzene "bottoms" sulfonic acids are the material left over after the removal of dodecyl benzene sulfonic acids that are used for household detergents.

The phosphorus-containing acids useful in making the basic metal salts of the present invention include any phosphorus acids such as phosphoric acid or esters; and thiophosphorus acids or esters, including mono and dithiophosphorus acids or esters. Preferably, the phosphorus acids or esters contain at least one, preferably two, hydrocarbyl groups containing from 1 to 50 carbon atoms, typically 1 to 30, preferably 3 to 18, more preferably 4 to 8.

In one embodiment, the phosphorus-containing acids are dithiophosphoric acids which are readily obtainable by the reaction of phosphorus pentasulfide ($P_2S_5$) and an alcohol or a phenol. Oxygen-containing analogs of these acids are conveniently prepared by treating the dithioic acid with water or steam which, in effect, replaces one or both of the sulfur atoms with oxygen.

In another embodiment, the phosphorus-containing acid is the reaction product of a polyalkene and phosphorus sulfide.

The phosphorus-containing acids useful in the present invention are described in U.S. Pat. No. 3,232,883 issued to Le Suer.

Phenols useful in making the basic metal salts of the invention are generally those which contain at least one hydrocarbyl substituent having at least 8 aliphatic carbon atoms. While the term "phenol" is used herein, it is to be understood that this term is not intended to limit the aromatic group of the phenol to benzene. Accordingly, it is to be understood that the aromatic group can be mononuclear such as a phenyl, a pyridyl, or a thienyl, or polynuclear.

All these acid materials suitable for use in making the overbased salts are well known in the art and have been described in detail in numerous publications.

The process of the present invention also includes the use of a promoter. A promoter is a material or mixture of materials employed to facilitate the incorporation of metal into the basic metal compositions. Although many materials have been used as promoters, among the more efficient, and those which are specifically contemplated by the present invention, are alcohols. Examples of alcohols include methanol, ethanol, isopropanol, dodecanol, behenyl alcohol, ethylene glycol, monomethyl ether of ethylene glycol, hexamethylene glycol, glycerol, pentaerythritol, benzyl alcohol, phenylethyl alcohol, aminoethanol, cinnamyl alcohol, allyl alcohol, and the like. Especially useful are the monohydric alcohols having up to 10 carbon atoms and mixtures of methanol with higher monohydric alcohols, in particular alcohols having at least 4 carbon atoms, such as isobutyl alcohol or amyl alcohol. In a preferred embodiment the alcohol is methanol or more preferably a mixture of isobutyl alcohol and amyl alcohol or a mixture of isobutyl alcohol and amyl alcohol with methanol. In such mixtures the methanol comprises 0 to 100 percent or preferably 20 to 80 percent by weight of the alcohol mixture.

Varying amounts of water may also be present in the alcohol mixture. Indeed, the presence of a certain amount of water is practically unavoidable, since water will be a byproduct of the reaction of neutralization of the acid material by the calcium base. Generally, however, water will not form a major part of the alcohol or alcohol mixture. It is normally desirable to minimize the water content when a carbonation step is included, as described below. This is not so important, however, if non-carbonated products are desired, and particularly if the desired degree of overbasing is low.

The preferred amount of the alcohol or mixture of alcohols is at least 0.5 equivalents per equivalent of the oil-soluble acid material. The upper limit of the amount of alcohol in the composition is not normally critical; in some instances a practical limit of 30% of the total reaction mixture is appropriate; sometimes 20% is preferred. That amount may correspond approximately to the amount which can lead to undesirable crystallization of calcium carbonate formed when carbon dioxide is used as a component of the reaction mixture (explained in more detail below).

A second part of the promoter is the so-called co-promoter. In certain prior art publications, calcium chloride is disclosed as a co-promoter. In the present invention, however, the co-promoter is an inorganic calcium salt other than chloride which is soluble in the alcohol or alcohol mixture, or an acid or salt which forms such a salt when treated with a calcium base. Suitable salts include the nitrate, bromide, iodide, halogenates (such as chlorate, bromate, iodate), cyanate, thiocyanate, thiosulfate, dithionate, permanganate, chromate, selenate, ferrocyanate, and ferricyanate of calcium. Preferable salts include calcium nitrate, calcium cyanate, calcium thiocyanate, calcium thiosulfate, and calcium dithionate. Illustrative acids which form such salts when treated with a calcium base (or which can be generated in situ to form such acids which in turn form salts) are nitric acid, hydrobromic acid, hydroiodic acid, chloric acid, bromic acid, iodic acid, cyanic acid, thiocyanic acid, thiosulfuric acid, permanganic acid, chromic acid, and selenic acid. Suitable salts which form such acids when treated with a calcium base or which may react directly to form the desired calcium salts include especially the ammonium salts.

The amount of the co-promoter is generally 0.1% to 10% by weight of the acid material described above; a preferable amount is 0.2% to 5% by weight.

The acid material described above is neutralized with a calcium base. Typical calcium bases include calcium oxide, calcium hydroxide, calcium alkoxides, calcium carbide, calcium hydride, and mixtures thereof. The preferred calcium base is calcium oxide or hydroxide, and most preferably calcium hydroxide. If the acid material is a particularly weak acid (such as an amide), one of the stronger calcium bases would be preferred. The calcium base can be supplied in powder or pellet form or in solution or suspension in the promoter system or other medium.

In order to prepare an overbased material, the amount of calcium base should be more than the theoretical amount required to neutralize the acid material. Thus 1.1 to 50 equivalents of calcium base will normally be used, per equivalent of acid material. Preferably the amount of calcium base will be 1.3 to 30 equivalents and often 1.5 to 20 equivalents.

The amount of excess metal (in this case calcium) is commonly expressed in terms of metal ratio. The term "metal ratio" is the ratio of the total equivalents of the metal to the equivalents of the acid compound. A neutral metal salt has a metal ratio of one. A salt having 4.5 times as much metal as present in a normal salt will have metal excess of 3.5 equivalents, or a ratio of 4.5. The basic salts of the present invention thus normally have a metal ratio of about 1.1 to 50, preferably 1.3 to 30, and sometimes 1.5 to 20, 3 to 25, or even 7 to 20.

In the simplest embodiment of the present invention, the overbasing process comprises simply mixing the above-described materials together in a suitable vessel such as a reaction flask, resin kettle, reaction tank, or reactor. Normally for ease of handling, reduction of viscosity, ease of agitation, or reduction of polarity of the reaction mixture, a certain amount of diluent oil or other inert solvent or dispersant is present. (If the reaction medium becomes too polar, for example, subsequent carbonation can lead to formation of a separate phase of metal carbonate, which is not normally desired.) Suitable diluents can be either oil or a strippable hydrocarbon or some other non-polar or low-polar diluent, such as $CCl_4$. Under the reaction conditions of this simple embodiment, the presence of the promoter and co-promoter provide sufficient solubility of the calcium base that it is able to more efficiently interact with the acid material to form the overbased material.

For even more efficient formation of the overbased material, however, it is customary to supply the above mixture with an acidic gas which further interacts to provide a composition with unique properties. Suitable acidic gases include carbon dioxide, sulfur dioxide, and sulfur trioxide, and of these carbon dioxide is preferred. Reaction with carbon dioxide is often referred to a carbonation.

The carbonation of the basic metal compositions made by the present process is effected preferably in a fluid solvent such as a hydrocarbon oil, at a temperature from room temperature to the boiling point of the mixture. If the carbonation is conducted under pressure, the boiling point of the mixture is raised, which can lead to a wider range of suitable temperatures. Ordinarily the carbonation temperature is below about 100° C. The presence of a small amount of water in the carbonation reaction is sometimes desirable to prevent excessive thickening of the mixture. The water may be added to the mixture or formed in situ by the neutralization of the organic acid with the calcium base. Carbonation may be accomplished simply by introducing carbon dioxide into the reaction mixture. After carbonation, the alcoholic promoting agent, to the extent that it is a volatile material, may be removed from the product by distillation. Alternatively, it may be allowed to remain in the product. The co-promoter will normally be allowed to remain in the product. Water which is used or formed during the reaction may be separated from the product by distillation or evaporation.

Significant physical changes normally take place in the overbased material as a result of carbonation. Upon mixing of the components before carbonation, the acid material forms a calcium salt with the calcium base so that the mixture contains a metal salt of the acid and a large excess of the calcium base. Such a mixture is ordinarily heterogeneous primarily because of the presence of the large excess of the sparingly soluble calcium base, the presence of the promoter materials notwithstanding. As carbonation proceeds the calcium base becomes solubilized in the organic phase and the carbonated product eventually becomes homogeneously dispersed in the organic phase. (This homogenization normally requires the presence of hydrocarbon oil or other solvent. A separate aqueous or alcoholic phase may remain, which may be removed). The homogeneous composition contains an unusually large amount of metal. The mechanism of the formation of the homogeneous product is not fully understood. It is believed, however, that carbonation converts the excess metal base to a carbonate or bicarbonate which forms with the metal salt of the acid material a homogeneous complex. The complex is readily soluble in hydrocarbon solvents such as benzene, xylene, or mineral oil. However, it is not always necessary for all of the metal base present in the process mixture to be so converted by carbonation in order to produce a soluble homogeneous product. In some cases a homogeneous product is obtained when as little as 75% of the excess calcium base is carbonated.

The carbonation may also be carried out in other solvents such as n-hexane, naphtha, decane, dodecane, benzene, toluene, xylene diphenylether, chlorobenzene, or any other fluid inert solvent. This solvent can be later removed by stripping if desired.

Examples of the carbonation reaction are provided in U.S. Pat. No. 3,256,156, Greenwald, except that for the process of the present invention calcium chloride is not used as a co-promoter. One or more of the co-promoters set forth above are used instead.

As used herein, the term "hydrocarbyl substituent" or "hydrocarbyl group" means a group having a carbon atom directly attached to the remainder of the molecule and having predominantly hydrocarbon character. Such groups include hydrocarbon groups, substituted hydrocarbon groups, and hetero groups, that is, groups which, while primarily hydrocarbon in character, contain atoms other than carbon present in a chain or ring otherwise composed of carbon atoms.

EXAMPLES

Example 1

An overbased material is prepared in a 3 L flask equipped with stirrer, thermowell, thermometer, subsurface inlet valve, and a cold water condenser. To the flask is added 727 g oil ("100 neutral"), 71 g of polyisobutylene (940 number average molecular weight) substituted succinic anhydride, 84 g of isobutyl alcohol/amyl alcohol mixture in about a 1:1 weight ratio, and 53 g calcium hydroxide. A mixture of 2.38 g calcium hydroxide and 5.6 nitric acid (70%) in 18 g water is separately prepared and added to the flask. To this mixture is added slowly a total of 617 g of monoalkylbenezenesulfonic acid having a number average molecular weight of about 480, about 85% active ingredient with about 15% unsulfonated alkylates, maintaining a temperature during the addition below 80° C. The mixture is heated to 150° C. to dry, then cooled to room temperature to about 50° C. To the mixture is added, with stirring, 53 g of the reaction product of heptyl phenol, lime, and formaldehyde (i.e. a calcium salt of methylene coupled alkylphenols) including about 65% diluent oil, 167 g methanol, and 84 g of i-butyl alcohol/amyl alcohol mixture, maintaining a temperature of 48°-52° C.

To this mixture is added a charge of 206 g calcium hydroxide followed by addition of carbon dioxide to a direct base number (DBN) of 45. (The DBN measures the strong base component of the composition and is determined by titration to phenolphthalein neutral point of a sample of the reaction mixture dissolved in isopropanol/toluene solvent with added water/sugar solution. It is expressed as KOH equivalents.) Two additional charges of calcium hydroxide are added, each of 103 g, followed in each case by addition of carbon dioxide. Carbon dioxide addition is discontinued when the DBN of the mixture is 45-55.

The mixture is heated to 150° C. under distillation conditions with nitrogen sweep and held at that temperature for one hour to remove volatile materials. The mixture is passed through a filter using diatomaceous earth filter aid, yielding the overbased product as the filtrate.

Example 2

An overbased material is prepared in the equipment of Example 1. To the flask is added 819 g oil ("100 neutral"), 168 g of the mixture of isobutyl and amyl alcohols of Example 1, and 90 g calcium hydroxide. A mixture of 12.6 g calcium hydroxide and 30.8 g nitric acid (70%) in 18 g water is separately prepared and added to the flask. To this mixture is added slowly a total of 982 g of the alkylbenzenesulfonic acid of Example 1, maintaining a temperature during the addition below 77° C. The mixture is heated with stirring to 85°-88° C. for 2 hours, and thereafter to 150° C. under distillation condition. Thereafter it is held at 150° C. with nitrogen sweep to remove residual alcohols. The product is filtered.

Example 3

Example 1 is substantially repeated except that in place of the solution of calcium hydroxide plus nitric acid in water, a solution of 4.75 g $(NH_4)_2S_2O_3$ in water is added. The final addition of calcium hydroxide is in four increments of 103 g, the additions followed by addition of carbon dioxide over 30, 63, 63, and 78 minutes, respectively, at a rate of 0.028 m³ (1 standard cubic foot) per hour until the desired phenolphthalein DBN of 45-55 is obtained. The mixture is stripped and filtered.

Example 4

Example 3 is substantially repeated except that NH₄SCN (4.9 g) is used in place of the (NH₄)₂S₂O₃.

Example 5

To the flask of Example 1 is added 802 g oil ("100 neutral"), 168.3 g of the isobutyl and amyl alcohol mixture of Example 1, and a solution of 7.6 g NH₄SCN in 11.8 g water. To the flask is added 90 g of calcium hydroxide, with stirring. Monoalkylbenezenesulfonic acid having a number average molecular weight of about 500, about 85% active ingredient with about 15% unsulfonated alkylates, 1000 g, is added slowly, maintaining a temperature below 77° C. The mixture is heated to 85°-88° C. and maintained for 2 hours, thereafter heated to 155° C. and nitrogen stripped. The product is filtered.

Example 6

Example 5 is repeated using 7.4 g (NH₄)₂S₂O₃ in place of the NH₄SCN.

Example 7

Example 1 is substantially repeated except that the added acidic gas is sulfur dioxide.

Example 8

Example 1 is substantially repeated except that the added acidic gas is sulfur trioxide.

Example 9

Example 1 is substantially repeated except that the monoalkylbenzenesulfonic acid is replaced with an equivalent amount of stearic acid.

Example 10

Example 1 is substantially repeated except that the monoalkylbenzenesulfonic acid is replaced with an equivalent amount of the reaction product of a polyalkene mixture and phosphorus sulfide, having a number average molecular weight of about 600.

Example 11

Example 1 is substantially repeated except that the monoalkylbenzenesulfonic acid is replaced with an equivalent amount of dodecylphenol.

Examples 12-17

Example 2 is substantially repeated except that in place of the 1:1 mixture of isobutyl and amyl alcohols is used an alcohol composition as shown below:

| Ex | Alcohol 1, % | Alcohol 2, % | Alcohol 3, % | Other, % |
|----|--------------|--------------|--------------|----------|
| 12 | methanol, 100 | | | |
| 13 | methanol, 80 | isobutyl alcohol, 10 | | water, 10 |
| 14 | methanol, 20 | isobutyl alcohol, 40 | amyl alcohol, 40 | |
| 15 | methanol, 10 | octyl alcohol, 89 | | water, 1 |
| 16 | benzyl alcohol, 20 | isobutyl alcohol, 80 | | |
| 17 | methanol, 30 | hexamethylene glycol, 70 | | |

In Example 14 the total amount of the alcohol mixture is 60 g; in Example 15 the total amount of the alcohol mixture is 800 g.

Example 18

Example 2 is substantially repeated except that in place of the 90 g calcium hydroxide, 68 g of calcium oxide is used.

Example 19

Example 1 is substantially repeated except that in place of the three charges of calcium hydroxide, five equal charges of calcium hydroxide are added totaling 1,163 g.

Example 20

Example 1 is substantially repeated except that the polyisobutylene substituted succinic anhydride is omitted and the alkylbenzenesulfonic acid is increased by an equivalent amount.

Example 21

An overbased material is prepared in a 3 L four-neck flask equipped with stirrer, thermowell, thermometer, subsurface inlet tube, and a cold water condenser. To the flask is added 494 g mineral oil, 59.5 g of polyisobutylene (940 number average molecular weight) substituted succinic anhydride, 18.6 g distilled water, 70.7 g of isobutyl alcohol/amyl alcohol mixture in about a 1:1 weight ratio, and 44.6 g calcium hydroxide. After stirring is started, 4.9 g nitric acid (70.9%) is charged to the flask and thereafter 620 g of the monoalkylbenzenesulfonic acid composition of Example 1 maintaining a temperature during the addition below 80° C. The mixture is heated to 150° C. for 20 minutes to dry, then cooled to room temperature.

The mixture is reheated, with stirring. An additional 70.7 g of the above isobutyl alcohol/amyl alcohol mixture is added, along with 140 g methanol and 44.1 g of the reaction product of heptyl phenol, lime, and formaldehyde (i.e. a calcium salt of methylene coupled alkylphenols) including about 65% diluent oil. An additional charge of 116 g calcium hydroxide is added followed by addition of carbon dioxide to a DBN of 37. A second increment of 116 g calcium hydroxide is charged, followed by addition of carbon dioxide to a DBN of 59. The addition of calcium hydroxide and carbon dioxide is repeated, to a DBN of 45.

The mixture is heated to 150° C. under distillation conditions with nitrogen sweep and held at that temperature for one half hour to remove volatile materials. The mixture is cooled and passed through a filter using diatomaceous earth filter aid, yielding the overbased product as the filtrate.

Each of the documents referred to above is incorporated herein by reference. Except in the Examples, or where otherwise explicitly indicated, all numerical quantities in this description specifying amounts of materials, reaction conditions, proportions, number of atoms, and the like, are to be understood as modified by the word "about." Unless otherwise indicated, each chemical or composition referred to herein should be interpreted as being a commercial grade material which may contain the isomers, byproducts, derivatives, and other such materials which are normally understood to be present in the commercial grade. As used herein, the expression "consisting essentially of" permits the inclusion of substances which do not materially affect the basic and novel characteristics of the composition under consideration.

What is claimed is:

1. A process for preparing an overbased calcium salt, comprising mixing together:
   (A) an oil-soluble acid material;
   (B) a promoter comprising:
      (i) an alcohol or alcohol mixture, and
      (ii) an inorganic calcium salt other than a halide which is soluble in the alcohol mixture of (i), or an acid or salt which forms said inorganic calcium salt when treated with a calcium base; and
   (C) greater than 1 equivalent of a calcium base per equivalent of oil-soluble acid material.

2. The process of claim 1 further comprising the step of reacting the mixture with an acidic gas selected from the group consisting of carbon dioxide, sulfur dioxide, and sulfur trioxide.

3. The process of claim 2 wherein the acid gas is carbon dioxide.

4. The process of claim 2 wherein the reaction with the acidic gas is conducted at a temperature of about 25° C. to the boiling point of the mixture.

5. The process of claim 1 wherein the acid material of (A) is selected from the group consisting of carboxylic acids, sulfonic acids, thiosulfonic acids, phosphorus-containing acids, and aromatic hydroxy compounds.

6. The process of claim 5 wherein the acid material of (A) is a sulfonic acid.

7. The process of claim 1 wherein the alcohol or alcohol mixture includes methanol.

8. The process of claim 1 wherein the alcohol or alcohol mixture includes at least one aliphatic alcohol having at least 4 carbon atoms.

9. The process of claim 8 wherein the aliphatic alcohol includes isobutyl alcohol or amyl alcohol.

10. The process of claim 9 wherein the alcohol or alcohol mixture of (B)(i) is a mixture of methanol, isobutyl alcohol, and amyl alcohol.

11. The process of claim 10 wherein the methanol comprises 0 to 100 percent by weight of the alcohol mixture.

12. The process of claim 11 wherein the methanol comprises about 20 to about 80 percent by weight of the alcohol mixture.

13. The process of claim 1 wherein the amount of the alcohol or mixture of alcohols of (B)(i) is at least about 0.5 equivalents per equivalent of oil-soluble acid material.

14. The process of claim 1 wherein the material of (B)(ii) is the nitrate, cyanate, thiocyanate, thiosulfate, or dithionate of calcium or acids or salts which form said calcium salts when treated with a calcium base.

15. The process of claim 14 wherein the material of (B)(ii) is an ammonium salt.

16. The process of claim 14 wherein the material of (B)(ii) is calcium nitrate or nitric acid.

17. The process of claim 1 wherein the amount of the substance of (B)(ii) is about 0.1% to about 10% of the weight of the acid material of (A).

18. The process of claim 1 wherein the calcium base of (C) is calcium hydroxide.

19. The process of claim 1 wherein the amount of the calcium base is about 1.1 to about 50 equivalents per equivalent of the oil soluble acid material of (A).

20. The process of claim 19 wherein the amount of the calcium base is about 1.3 to about 30 equivalents per equivalent of the oil soluble acid material of (A).

* * * * *